United States Patent [19]

Nedelec et al.

[11] 4,242,355

[45] * Dec. 30, 1980

[54] NOVEL 3-(AMINOETHYL)-PHENOLS

[75] Inventors: Lucien Nedelec, Le Raincy; Daniel Frechét, Paris; Claude Dumont, Nogent-sur-Marne, all of France

[73] Assignee: Roussel Uclaf, Paris, France

[*] Notice: The portion of the term of this patent subsequent to Dec. 19, 1995, has been disclaimed.

[21] Appl. No.: 76,486

[22] Filed: Sep. 17, 1979

[30] Foreign Application Priority Data

Sep. 22, 1978 [FR] France .................................. 78 27190

[51] Int. Cl.³ .................... A61K 31/38; A61K 31/135; C07D 333/16; C07C 87/29
[52] U.S. Cl. ..................................... 424/275; 424/330; 549/75; 564/336
[58] Field of Search ................. 549/75; 424/275, 330; 260/570.8 R, 570.9

[56] References Cited

U.S. PATENT DOCUMENTS 2,525,674  10/1950  Heinzelmann ........................ 549/75
4,130,658  12/1978  Nedelec et al. ..................... 424/308

Primary Examiner—Alan Siegel
Attorney, Agent, or Firm—Hammond & Littell, Weissenberger and Muserlian

[57] ABSTRACT

Novel derivatives of 3-(aminoethyl)-phenols of the formula

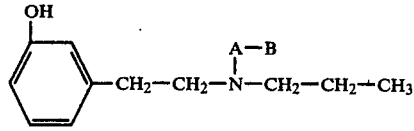

wherein A is a simple bond or alkylene of 1 to 6 carbon atoms and B is selected from the group consisting of aryl, diarylmethyl, cycloalkyl of 3 to 10 carbon atoms and heteroaryl with the proviso that B is not phenyl when A is ethylene and their non-toxic, pharmaceutically acceptable acid addition salts having a dopaminergic activity and their preparation.

17 Claims, No Drawings

NOVEL 3-(AMINOETHYL)-PHENOLS

STATE OF THE ART

U.S. Patent Application Ser. No. 905,535 filed May 12, 1978, now U.S. Pat. No. 4,175,136, U.S. Pat. No. 4,130,658 and No. 2,525,674 and French Pat. No. 1,397,429 which corresponds to U.S. Pat. No. 3,377,359, describe compounds with related activity.

OBJECTS OF THE INVENTION

It is an object of the invention to provide the novel compounds of formula I and their non-toxic, pharmaceutically acceptable acid addition salts and a novel process and intermediates for their preparation.

It is another object of the invention to provide dopaminergic compositions and to provide a novel method of inducing dopaminergic activity in warm-blooded animals.

These and other objects and advantages of the invention will become obvious from the following detailed description.

THE INVENTION

The novel compounds of the invention are selected from the group consisting of 3-(aminoethyl)-phenols of the formula

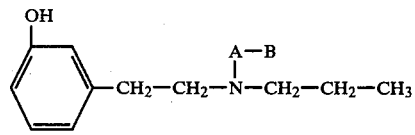

wherein A is a simple bond or alkylene of 1 to 6 carbon atoms and B is selected from the group consisting of aryl, diarylmethyl, cycloalkyl of 3 to 10 carbon atoms and heteroaryl with the proviso that B is not phenyl when A is ethylene and their non-toxic, pharmaceutically acceptable acid addition salts.

Examples of alkylene radicals of A are methylene, ethylene, propylene, trimethylene, tetramethylene, pentamethylene and hexamethylene. Example of B are aryl such as phenyl, naphthyl and anthracenyl; diarylmethyl such as benzhydryl; cycloalkyl of 3 to 10 carbon atoms such as cyclopentyl, cyclohexyl, cycloheptyl and adamantyl; and heteroaryl such as thienyl, indolyl, imidazolyl, pyrrolyl and pyridyl.

Examples of suitable acids for the non-toxic, pharmaceutically acceptable acid addition salts are inorganic acids such as hydrochloric acid, hydrobromic acid, hydroiodic acid, nitric acid, sulfuric acid or phosphoric acid and organic acids such as acetic acid, formic acid, benzoic acid, maleic acid, fumaric acid, succinic acid, tartaric acid, citric acid, oxalic acid, glyoxylic acid, asparatic acid, alkanesulfonic acids such as methane sulfonic acid or ethane sulfonic acid, aryl sulfonic acids such as benzene sulfonic acid or p-toluene sulfonic acid and aryl carboxylic acids.

Among the preferred compounds of formula I are those wherein B is phenyl, cyclopentyl, cyclohexyl, adamantyl, thienyl, indolyl or imidazolyl and their non-toxic, pharmaceutically acceptable acid addition salts, those wherein A is a simple bond or alkylene of 2 to 3 carbon atoms and B is phenyl, cyclopentyl, cyclohexyl, adamantyl, thienyl, indolyl and imidazolyl and especially those wherein A-B is phenylpropyl, cyclohexylethyl, cyclopentyl, adamantyl, 2-(2-thienyl)-ethyl, 2-[1H-indol-3-yl]-ethyl or 2-[1H-imidazol-4-yl]-ethyl and their non-toxic, pharmaceutically acceptable acid addition salts.

Specific preferred compounds of the invention are di-[3-{2-[(3-phenylpropyl]-propylamino)-ethyl}-phenol]-oxalate, 3-[2-(propyl)-2-(2-thienyl)-ethylamino]-ethyl-phenol hydrochloride, 3-[2-{(2-cyclohexylethyl)-propylamino}-ethyl]-phenol hydrochloride and 3-[2-(cyclopentylpropylamino)-ethyl]-phenol hydrochloride.

The novel process of the invention for the preparation of a compound of formula I comprises subjecting a compound of the formula

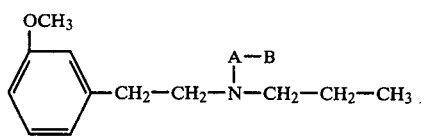

wherein A and B have the above definition to hydrolysis to obtain the corresponding compound of formula I which may be salified, if desired.

Preferably, the hydrolysis of the compound of formula II is effected with concentrated hydrobromic acid or pyridine hydrochloride at reflux. The hydrolysis is advantageously followed by alkalinization with ammonium hydroxide to obtain the free base of formula I. To form the acid addition salts, approximately equimolar amounts of the compound of formula I and the acid are reacted.

The novel dopaminergic compositions are comprised of a dopaminergically effective amount of at least one compound of formula I and their non-toxic, pharmaceutically acceptable acid addition salts and an inert pharmaceutical carrier or excipient. The composition may be in the form of tablets, coated tablets gelules, capsules, granules, suppositories and injectable solutions or suspensions.

Examples of suitable excipients or pharmaceutical carriers are talc, arabic gum, lactose, starch, magnesium stearate, cacao butter, aqueous and non-aqueous vehicles, fatty bodies of animal or vegetable origin, paraffinic derivatives, glycols, preservatives, diverse wetting agents, emulsifiers or dispersants.

The compositions of the invention possess remarkable susceptible dopaminergic properties making them useful for treating neurological syndromes of extrapyramidal origin and inhibiting the secretion of prolactin. They are useful for treatment of the symptoms of Parkinson disease, treatment of post-encephalitic parkinson syndromes and of arteriosclerous origin or toxic etiology as well as treating troubles of hyperprolactinemia.

Among the preferred compositions of the invention are those wherein B is phenyl, cyclopentyl, cyclohexyl, adamantyl, thienyl, indolyl or imidazolyl and their non-toxic, pharmaceutically acceptable acid addition salts, those wherein A is a simple bond or alkylene of 2 to 3 carbon atoms and B is phenyl, cyclopentyl, cyclohexyl, adamantyl, thienyl, indolyl and imidazolyl and especially those wherein A-B is phenylpropyl, cyclohexylethyl, cyclopentyl, adamantyl, 2-(2-thienyl)-ethyl, 2-[1H-indol-3-yl]-ethyl or 2-[1H-imidazol-4-yl]-ethyl and their non-toxic, pharmaceutically acceptable acid addition salts.

Specific preferred compositions of the invention are di-[3-{2-[(3-phenylpropyl]-propylamino)-ethyl}-phenol]-oxalate, 3-[2-(propyl)-2-(2-thienyl)-ethylamino]-ethyl-phenol hydrochloride, 3-[2{-(2-cyclohexylethyl)-propylamino}-ethyl]-phenol hydrochloride and 3-[2-(cyclopentylpropylamino)-ethyl]-phenol hydrochloride.

The novel method of the invention for treating the syndromes of Parkinson disease in warm-blooded animals including humans comprises administering to warm-blooded animals a dopaminergically effective amount of at least one compound of formula I and its non-toxic, pharmaceutically acceptable acid addition salts. The compounds may be administered orally, rectally or parenterally and the usual daily dose is 0.2 to 10 mg/kg by oral route in man.

The compounds of formula II wherein A is alkylene of 1 to 3 carbon atoms and B has the above definition may be prepared by reacting a compound of the formula

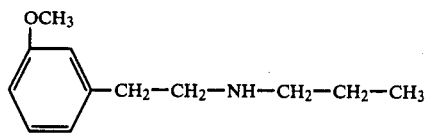  III with a halide of the formula

  IV wherein A and B have the above definition and Hal is a chlorine bromine, or iodine atom. The reaction is preferably effected in an alkanol such as ethanol in the presence of an alkaline agent such as sodium carbonate or potassium carbonate or in the presence of an organic base such as triethylamine at reflux.

The compounds of formula II wherein A is alkylene of 2 to 6 carbon atoms may be prepared by reacting the compound of formula III with an acid of the formula

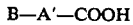  V wherein B has the above definition and A' is alkylene of 1 to 5 carbon atoms to form a compound of the formula

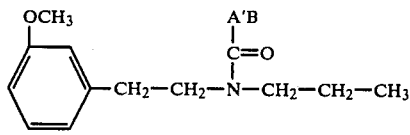  VI and reducing the latter to the corresponding compound of formula II.

The reaction of the compounds of formula III and V is preferably effected at reflux in the presence of dicyclohexylcarbodiimide. The reduction of the compound of formula VI is preferably effected with lithium aluminum hydride or diborane or a complex of diborane and dimethylsulfide in an organic solvent such as tetrahydrofuran.

The compounds of formula II wherein A is alkylene of 2 to 6 carbon atoms may also be prepared by reacting a compound of the formula

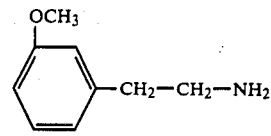  VII with an acid of formula V to obtain a compound of the formula

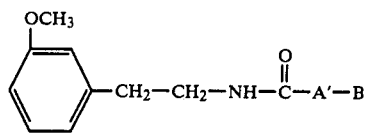  VIII reducing the latter to obtain a compound of the formula

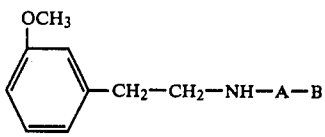  IX and reacting the latter with a propyl halide such as the chloride, bromide or iodide to obtain the corresponding compound of formula II.

The condensation with the acid of formula V and the reduction step may be effected as described previously. The reaction of the compound of formula IX with the propyl halide is preferably effected in an organic solvent such as acetone or methyl ethyl ketone in the presence of an alkaline agent such as potassium carbonate at reflux temperatures.

The products of formula II may also be prepared by reacting the acid of the formula

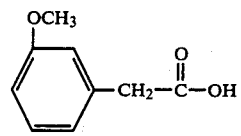  X with an amine of the formula

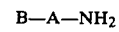  XI wherein B and A have the above definitions to obtain a compound of the formula

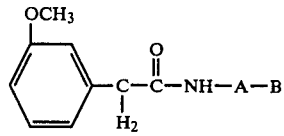  XII reducing the latter to form a compound of formula IX and reacting the latter as above. The reduction is preferably effected with lithium aluminum hydride.

The compounds of formula III may be prepared by reacting the compound of formula VII with a propyl halide or by reacting a compound of formula VII with propionic acid to obtain a compound of the formula

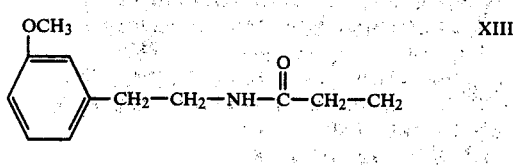

and reducing the latter.

The novel intermediates of the invention are those of formula II.

In the following examples there are described several preferred embodiments to illustrate the invention. However, it should be understood that the invention is not intended to be limited to the specific embodiments.

EXAMPLE 1 di-[3-{2-[(3-phenylpropyl)-propylamino]-ethyl}-phenol]oxalate

STEP A: 3-methoxy-N-propyl-benzeneethanamine

A mixture of 10 g of 3-methoxy-benzeneethanamine, 11.25 g of 1-iodopropane and 66 ml of triethylamine was refluxed with stirring under an inert atmosphere for 90 minutes and was then distilled to dryness under reduced pressure. 250 ml of 0.5 N ammonium hydroxide solution were added to the residue and the mixture was extracted with ethyl acetate. The organic phase was washed with water, dried and evaporated to dryness under reduced pressure to obtain 12.1 g of an oil. The latter was chromatographed over silica gel and was eluted with a 7-3 chloroform-methanol mixture to obtain 8 g of product. The latter was dissolved in 20 ml of ethyl acetate and an ethyl acetate solution saturated with hydrogen chloride was added thereto dropwise until a pH of 1 was reached. Crystallization occurred and the mixture was vacuum filtered to obtain 7.2 g of 3-methoxy-N-propyl-benzeneethanamine hydrochloride melting at 182° C.

STEP B:
N-[2-(3-methoxyphenyl)-ethyl]-N-propylbenzene-propanamine

A stirred suspension of 6 g of the product of Step A, 12 g of 3-phenylpropyl bromide, 12 g of potassium carbonate and 100 ml of acetone under nitrogen was refluxed for 40 hours and was then cooled to room temperature and poured into 500 ml of water. The mixture was extracted with methylene chloride and the organic phase was dried and evaporated to dryness under reduced pressure to obtain 12 g of a yellow oil. The latter was taken up in 1 N hydrochloric acid and the mixture was washed with ether and made alkaline by addition of sodium hydroxide at about 10° C. The resulting precipitate was extracted with methylene chloride and the organic phase was dried and evaporated to dryness under reduced pressure to obtain 9.5 g of N-[2-(3-methoxyphenyl)-ethyl]-N-propylbenzenepropanamine in the form of a yellow oil which was used as is for the next step.

STEP C:
di-[3-{2-[(3-phenylpropyl)-propylamino]-ethyl}-phenol] oxalate

A stirred mixture of 9.5 g of the product of Step B in 50 ml of 48% hydrobromic acid was refluxed under an inert atmosphere for 90 minutes and the mixture was cooled to 20° C. and was make alkaline with concentrated ammonium hydroxide. The mixture was extracted with methylene chloride and the organic phase was dried and evaporated to dryness under reduced pressure to obtain 9 g of a yellow oil residue. The residue was dissolved in 10 ml of methanol and 1.9 g of oxalic acid dihydrate were added thereto. The mixture was heated to 40° C. until dissolution occured and 50 ml of ethyl acetate were added thereto. The mixture was concentrated to a volume of 50 ml and was vacuum filtered to obtain 6.5 g of di-[3-{2-[(3-phenylpropyl)-propylamino]-ethyl}-phenol] oxalate melting at 145° C. The product was dissolved in 60 ml of methanol and the solution was filtered. 100 ml of ethyl acetate were added to the filtrate and the mixture was concentrated to 60 ml and was vacuum filtered to obtain 5.5 g of the product melting at 145° C.

Analysis: $(C_{20}H_{27}NO)_2.(COOH)_2$; molecular weight = 684.88: Calculated: %C 73.65; %H 8.24; %N 4.09; Found: %C 73.5; %H 8.4; %N 3.8

UV Spectrum (ethanol):
Inflex.—215 nm $E_1^1=367$
Inflex.—223 nm $E_1^1=184$
Inflex.—268 nm $E_1^1=51$
Max.—273 nm $E_1^1=61$ $\epsilon=2100$
Inflex.—279 nm $E_1^1=55$ U.V. Spectrum (ethanol - N/10 NaOH):
Max.—240 nm $E_1^1=289$ $\epsilon=9900$
Inflex.—269 nm $E_1^1=38$
Max.—290-291 nm $E_1^1=98$ $\epsilon=3350$

EXAMPLE 2

3-[2-propyl-2-(2-thienyl)-ethylamino]-ethyl-phenol hydrochloride

STEP A:
N-[2-(3-methoxyphenyl)-ethyl]-2-thiophene-acetamide

A mixture of 15.1 g of 3-methoxy-benzeneethanamine and 14.2 g of α-thienylacetic acid was stirred at 200° C. under an inert atmosphere for 30 minutes and was then cooled to 20° C. 600 ml of a refluxing 1-1 ether-isopropyl ether mixture were added thereto and the mixture was filtered. The filtrate was evaporated to dryness under reduced pressure to obtain 28 g of a brown oil. The oil was crystallized from 28 ml of ether at 5° C. and the mixture was vacuum filtered to obtain 25.5 g of N-[2-(3-methoxyphenyl)-ethyl]-2-thiopheneacet amide melting at 50° C.

STEP B:
N-[2-(3-methoxyphenyl)-ethyl]-2-thiophenethanamine hydrochloride 21.9 ml of a complex of borane-dimethylsulfide were added all at once at room temperature to a solution of 21.90 g of the product of Step A in 219 ml of anhydrous tetrahydrofuran and the mixture was progressively heated to reflux and held at reflux for one hour. The mixture was cooled to 5° C. and 100 ml of 2 N hydrochloric acid were cautiously added thereto. The mixture was refluxed for one hour and the tetrahydrofuran was then distilled under reduced pressure. 300 ml of water were added thereto and the mixture was washed with ether. The organic phase was made alkaline with concentrated ammonium hydroxide and was extracted with methylene chloride. The organic phase was dried and evaporated to dryness under reduced pressure to obtain 21.5 g of yellow oil residue. The oil was dissolved in 50 ml of water and a solution of hydrogen chloride in ethyl acetate was added to the solution until the pH was 2. The mixture was vacuum filtered and the recovered product was washed with ether to obtain 21.70 g of N-[2-(3-methoxyphenyl)-ethyl]-2-thiophene-ethanamine hydrochloride melting at 170° C.

Analysis: $C_{15}H_{19}NOS.HCl$; molecular weight=297.84: Calculated: %C 60.48; %H 6.77; %N 4.70; %Cl 11.95; %C 10.76; Found: %C 60.6; %H 6.8; %N 4.5; %Cl 12.0; %C 10.6

UV Spectrum (ethanol):
Max.—224 nm  $E_1^1=435$  $\epsilon=13,000$
Inflex.—234 nm  $E_1^1=283$
Max.—274 nm  $E_1^1=65$  $\epsilon=1,950$
Max.—280–281 nm  $E_1^1=60$  $\epsilon=1,800$ IR Spectrum ($CHCl_3$): Absorption in general region-aromatic at 1605, 1589, 1490 $cm^{-1}$ STEP C:
N-[2-(3-methoxyphenyl)-ethyl]-N-propyl-2-thiophene-ethanamine A stirred mixture of 21.70 g of the product of Step B, 50 g of 1-iodopropane, 50 g of potassium carbonate and 400 ml of absolute ethanol was refluxed for 6¼ hours and the ethanol was distilled under reduced pressure. 500 ml of water and 50 ml of sodium hydroxide solution were added thereto and the mixture was extracted with methylene chloride. The organic phase was washed with aqueous sodium chloride solution, dried and evaporated to dryness under reduced pressure to obtain 22 g of N-[2-(3-methoxyphenyl)-ethyl]-N-propyl-2-thiophene-ethanamine which was used as is for the next step.

STEP D:
3-[2-propyl-2-(2-thienyl)-ethylamino]-ethyl-phenol hydrochloride

A stirred mixture of 21 g of the product of Step C, 42 ml of acetic acid and 42 ml of 48% hydrobromic acid was refluxed under an inert atmosphere for 5 hours and was then cooled. 500 ml of ice and then 100 ml of concentrated ammonium hydroxide were added to the mixture and the resulting mixture was extracted with methylene chloride. The organic phase was washed with aqueous sodium chloride solution, dried and evaporated to dryness under reduced pressure to obtain 21 g of oil residue. The oil was dissolved in 21 ml of isopropanol and a solution of hydrogen chloride in ethyl acetate was added thereto at 5° C. until the pH was 1. Crystallization was effected and the mixture was vacuum filtered. The recovered product was washed with isopropanol and then with ether to obtain 16.5 g of 3-[2-propyl-2-(2-thienyl)-ethylamino]-ethyl-phenol hydrochloride melting at ~140° C.

The said product was dissolved in 20 ml of methanol and 1.5 liters of methylene chloride at reflux and the solution was treated with activated carbon and was filtered. The filtrate was reduced to a volume of 50 ml and was then added to 300 ml of ethyl acetate. The mixture stood at room temperature for 2 hours and was then vacuum filtered. The recovered product was washed with ethyl acetate and dried at 90° C. under reduced pressure to obtain 14 g of product. The latter was dissolved in 400 ml of refluxing isopropanol and the mixture was filtered and reduced to a volume of 75 ml. After crystallization, the mixture was vacuum filtered and the 13 g of recovered product was taken up in 150 ml of refluxing ethanol. The mixture was filtered and the filtrate was reduced to a volume of 50 ml. After crystallization, the mixture was vacuum filtered and the recovered product was washed with ethanol, then ether and dried at 85° C. under reduced pressure to obtain 11.8 g of the said hydrochloride melting at 145° C.

Analysis: $C_{17}H_{23}NOS$. HCl; molecular weight=325.89: Calculated: %C 62.65; %H 7.42; %N 4.30; %Cl 10.88; %S 9.84; Found: %C 62.5; %H 7.6; %N 4.1; %Cl 11.0; %S 9.7

UV Spectrum (ethanol):
Max.—225 nm  $E_1^1=360$  $\epsilon=11,700$
Inflex.—235 nm  $E_1^1=258$
Max.—247 nm  $E_1^1=66$  $\epsilon=2,150$
Inflex.—278 nm  $E_1^1=61$ IR Spectrum (Nujol): associated OH at 3180 $cm^{-1}$; aromatic at 1615, 1590 and 1486 $cm^{-1}$.

UV Spectrum (ethanol—0.1 NaOH):
Max.—237 nm  $E_1^1=514$  $\epsilon=16,800$
Max.—290–291 nm  $E_1^1=98$  $\epsilon=3,200$

EXAMPLE 3

3-[2-{(2-cyclohexylethyl)-propylamino}-ethyl]-phenol hydrochloride

STEP A:
N-[2-(3-methoxyphenyl)-ethyl]-cyclohexane-acetamide

A stirred mixture of 20 g of 3-methoxy-benzeneethanamine and 15.2 g of cyclohexylacetic acid was heated at 190°–200° C. under an inert atmosphere for 45 minutes and was then cooled to 30° C. The product was dissolved in ethyl acetate and the solution was washed successively with N sodium hydroxide solution, N hydrochloric acid and water and was evaporated to dryness. The 29 g of oil residue was crystallized from petroleum ether (b.p.=40°–70° C.) and the product was dried to obtain 21.3 g of N-[2-(3-methoxyphenyl)-ethyl]cyclohexane-acetamide in the form of a white solid melting at 74° C.

STEP B:
N-(2-cyclohexylethyl)-3-methoxy-benzeneethanamine hydrochloride

A solution of 21.3 g of the product of Step A in 100 ml of tetrahydrofuran was added over 20 minutes at 0° C. to a suspension of 11.8 g of lithium aluminum hydride in 150 ml of tetrahydrofuran and the mixture was heated to reflux for 4 hours. After the addition of 6 g of lithium aluminum hydride thereto, the mixture was refluxed for another 6 hours. After 22 hours, 500 ml of tetrahydrofuran containing 20% water were added thereto at 20°–30° C. and the mixture was filtered. The filtrate was distilled and was then extracted with methylene chloride. The organic phase was washed with water, dried and evaporated to dryness. The 19.4 g of oil residue were dissolved in 100 ml of ethyl acetate and an excess of ethyl acetate containing hydrogen chloride was added thereto. The mixture was held in a refrigerator for one hour and was then vacuum filtered. The recovered product was washed with ethyl acetate and dried to obtain 20.6 g of N-(2-cyclohexylethyl)-3-methoxy-benzeneethanamine hydrochloride melting at 174° C.

STEP C:
N-(2-cyclohexylethyl)-3-methoxy-N-propyl-benzeneethanamine 48 g of potassium carbonate were added to a solution of 17.8 g of the product of Step B in 180 ml of acetone and after the addition of 17.5 ml of 1-iodopropane, the mixture was refluxed under an inert atmosphere for 4¼ hours and was filtered. The filtrate was evaporated to dryness and the residue was taken up in ether. 100 ml of 2 N sodium hydroxide solution was added to the mixture and the decanted organic phase was washed with water, dried and evaporated to dryness to obtain 19.25 g of N-(2-cyclohexylethyl)-3-methoxy-N-propyl-benzeneethanamine in the form of a yellow oil which was used as is for the next step.

STEP D:
3-[2-{(2-cyclohexylethyl)-propylamino}-ethyl]-phenol-hydrochloride

A stirred mixture of 19.25 g of the product of Step C in 95 ml of 48% hydrobromic acid was refluxed under an inert atmosphere for 90 minutes and was then cooled and made alkaline by addition of concentrated ammonium hydroxide. The mixture was saturated with sodium chloride and was extracted with ethyl acetate. The organic phase was washed with water, dried and evaporated to dryness. The 19 g of oil residue were dissolved in 50 ml of methyl ethyl ketone and an excess of ethyl acetate containing hydrogen chloride was added thereto. Crystallization was induced and the mixture was stored in a refrigerator overnight and was vacuum filtered. The recovered product was dried at 60° C. under reduced pressure to obtain 17.4 g of product which was crystallized twice from methyl ethyl ketone to obtain 16.35 g of 3-[2-{(2-cyclohexylethyl)-propylamine}-ethyl]-phenol hydrochloride melting at 100° C.

Analysis: $C_{19}H_{31}NO.HCl$; molecular weight=325.92: Calculated: %C 70.02; %H 9.90; %N 4.30; %Cl 10.88; Found: %C 70.0; %H 9.9; %N 4.2; %Cl 10.8

UV Spectrum (ethanol):
Max.—217 nm $E_1^1=184$ $\epsilon=6,000$
Max.—275 nm $E_1^1=64$ $\epsilon=2,100$
Inflex.—279 nm $E_1^1=59$ UV Spectrum (ethanol—0.1 N NaOH):
Max.—239 nm $E_1^1=285$ $\epsilon=9,300$
Max.—291 nm $E_1^1=98$ $\epsilon=3,200$

EXAMPLE 4

3-[2-(propyl-{tricyclo-(3,3,1,1$^{3-7}$)-decan-1-yl}-amino)-ethyl]-phenol hydrochloride STEP A:
3-methoxy-N-[tricyclo-(3,3,1,1$^{3-7}$)-decan-1-yl]-benzeneacetamide A mixture of 33.4 g of 3-methoxy-benzene acetic acid, 15 g of 1-amino-adamantane, 40 g of dicyclohexylcarbodiimide and 500 ml of ethyl acetate was stirred at room temperature under an inert atmosphere for one hour and was then filtered. The filter was washed with ethyl acetate and the filtrate was washed 3 times with 200 ml of N sodium hydroxide solution, twice with 200 ml of N hydrochloric acid and once with 200 ml of water. The filtrate was then dried and evaporated to dryness under reduced pressure to obtain 40 g of a yellow oil which was crystallized from 30 ml of isopropyl ether to obtain 22.2 g of crystalline 3-methoxy-N-[tricyclo-(3,3,1,1$^{3-7}$)-decan-1-yl]-benzene-acetamide melting at 116° C.

STEP B:
3-methoxy-N-[tricyclo-(3,3,1,1$^{3-7}$)-decan-1-yl]benzeneethanamine hydrochloride 22.2 g of the product of Step A were added over 5 minutes at 5° C. to a suspension of 9 g of lithium aluminum hydride hydride in 200 ml of tetrahydrofuran and the mixture was refluxed with stirring for 100 minutes and was then cooled to 10° C. 40 ml of tetrahydrofuran containing 50% of water were added dropwise to the mixture over 20 minutes and the mixture was filtered. The filtrate was evaporated to dryness and the 20 g of colorless oil residue were dissolved in 20 ml of ethyl acetate. A solution of ethyl acetate saturated with hydrogen chloride was added to the solution dropwise until the pH was 1 and the mixture was vacuum filtered to obtain 15 g of 3-methoxy-N-[tricyclo-(3,3,1,1$^{3-7}$)-decan-1-yl]-benzeneethanamine hydrochloride in the form of crystals melting at 226° C.

STEP C:
3-methoxy-N-propyl-N-[tricyclo-(3,3,1,1$^{3-7}$)-decan-1-yl]-benzeneethanamine hydrochloride A mixture of 8.7 g of the product of Step B, 10 g of 1-iodo-propane, 10 g of potassium carbonate was refluxed under an inert atmosphere for 2½ hours and was then cooled. The mixture was extracted 3 times with 100 ml of methylene chloride and the organic phase was washed twice with 100 ml of water, dried over magnesium sulfate and filtered. The filtrate was evaporated to dryness under reduced pressure to obtain 11.2 g of a yellow oil. The oil was chromatographed over silica gel and was crystallized to obtain 5.2 g of 3-methoxy-N-propyl-N-[tricyclo-(3,3,1,1$^{3-7}$)decan-1-yl]-benzeneethanamine hydrochloride melting at 174° C.

STEP D:
3-[2-(propyl-{tricyclo-(3,3,1,1$^{3-7}$)-decan-1-yl}amino)-ethyl]-phenol hydrochloride A stirred mixture of 10.4 g of the product of Step C and 104 ml of 48% hydrobromic acid was refluxed under an inert atmosphere for one hour and was then cooled and made alkaline with concentrated ammonium hydroxide. The mixture was extracted 3 times with 80 ml of methylene chloride and the organic phase was washed with 100 ml of water, dried over magnesium sulfate and filtered. The filtrate was evaporated to dryness and the 8.2 g of yellow oil residue was dissolved in 20 ml of ethyl acetate. A solution of ethyl acetate saturated with hydrogen chloride was added dropwise to the mixture until the pH was 1 and the mixture was vacuum filtered. The recovered product was successively crystallized from methanol and isopropanol and then methanol and ethyl acetate. The mixture was vacuum filtered to obtain 5.9 g of 3-[2-(propyl-{tricyclo-(3,3,1,1$^{3-7}$)-decan-1-yl}-amino)-ethyl]phenol hydrochloride melting at 220° C.

Analysis: $C_{21}H_{31}NO.HCl$; molecular weight=349.935: Calculated: %C 72.07; %H 9.22; %N 4.00; %Cl 10.13; Found: %C 72.2; %H 9.4; %N 3.9; %Cl 10.2

UV Spectrum (ethanol):
Max.—217 nm $E_1^1=185$ $\epsilon=6,500$
Max.—275 nm $E_1^1=62$ $\epsilon=2,150$
Inflex.—279 nm $E_1^1=56$ UV Spectrum (ethanol—0.1 NaOH):
Max—240 nm $E_1^1=267$ $\epsilon=9,300$
Max.—292 nm $E_1^1=90$ $\epsilon=3,150$

EXAMPLE 5

3-[2-(cyclopentylpropylamino)-ethyl]-phenol hydrochloride

STEP A:
N-cyclopentyl-3-methoxy-N-propyl-benzeneethanamine

A stirred mixture of 3.4 g of 3-methoxy-N-propyl-benzeneethanamine, 4 g of potassium carbonate and 15 ml of cyclopentyl bromide was refluxed for one hour after which 5 g of potassium carbonate were added thereto and the mixture was refluxed for another 3 hours. The mixture was poured into 50 ml of water and the mixture was extracted 3 times with 50 ml of ether. The organic phase was dried and filtered and the filtrate was evaporated to dryness to obtain 4.5 g of N-cyclopentyl-3-methoxy-N-propylbenzeneethanamine in the form of a red oil which was used as is for the next step.

STEP B: 3-[2-(cyclopentylpropylamino)-ethyl]-phenol hydrochloride

A stirred mixture of 4.35 g of the product of Step A and 43 ml of 48% hydrobromic acid was refluxed under a nitrogen atmosphere for 2 hours and the mixture was cooled and made alkaline by addition of concentrated ammonium hydroxide. The mixture was extracted 3 times with methylene chloride and the combined organic phases were washed twice with 50 ml of water, dried over magnesium sulfate and filtered. The filtrate was evaporated to dryness and the 4 g of brown oil residue were dissolved in 5 ml of methanol. A solution of ethyl acetate saturated with hydrogen chloride was added to the mixture dropwise until the pH was acidic and the mixture was vacuum filtered. The recovered product was crystallized from methanol and ethyl acetate to obtain 2.7 g of 3-[2-(cyclopentylpropylamino)-ethyl]-phenol hydrochloride melting at 140° C.

Analysis: $C_{16}H_{25}NO.HCl$; molecular weight=283.84
Calculated: %C 67.7; %H 9.23; %N 4.94; %Cl 12.49;
Found: %C 67.5; %H 9.5; %N 4.7; %Cl 12.7

UV Spectrum (ethanol):
    Max.—218 nm    $E_1^1=229$    $\epsilon=6,500$
    Max.—274 nm    $E_1^1=76$    $\epsilon=2,200$
    Inflex.—279 nm    $E_1^1=69$ UV Spectrum (ethanol—0.1 N NaOH):
    Max.—241-242 nm    $E_1^1=329$    $\epsilon=9,300$
    Max.—291 nm    $E_1^1=113$    $\epsilon=3,200$

EXAMPLE 6

3-[2-(2-{1H-imidazol-4-yl}-ethyl)-propylamino-ethyl]-phenol oxalate

STEP A:
3-methoxy-N-[2-(1H-imidazol-4-yl)-ethyl]-benzeneethanamine

A solution of 27.6 g of histamine dihydrochloride in 150 ml of 2 N sodium hydroxide was evaporated to dryness and the residue and 24.9 g of 3-methoxy-benzene acetic acid were stirred at 210° C. for 30 minutes and was then cooled to 50° C. One liter of refluxing ethyl acetate was added thereto and the mixture was filtered. The filtrate ws evaporated to dryness under reduced pressure and the residue was crystallized from methylene chloride to obtain 27.7 g of 3-methoxy-N-[2-(1H-imidazol-4-yl)-ethyl]-benzeneethanamine melting at 98° to 100° C.

STEP B:
N-[2-(3-methoxyphenyl)-ethyl]-1-H-imidazol-4-ethanamine dihydrochloride A stirred mixture of 5 g of the product of Step A, 2.5 g of lithium aluminum hydride and 50 ml of tetrahydrofuran was refluxed for 90 minutes and was then cooled to 10° C. 100 ml of tetrahydrofuran containing 20% water and 100 ml of methylene chloride were added thereto and the mixture was filtered. The filtrate was evaported to dryness and the 4.7 g of yellow oil residue were dissolved in 30 ml of isopropanol. A solution of ethyl acetate saturated with hydrogen chloride was added thereto to adjust the pH to 1 and the mixture was vacuum filtered. The recovered product was washed with isopropanol to obtain 3 g of N-[2-(3-methoxyphenyl)-ethyl]-1H-imidazol-4-ethanamine dihydrochloride in the form of brilliant colorless platelets melting at 195°-198° C.

STEP C:
N-[2-(3-methoxyphenyl)-ethyl]-N-propyl-1H-imidazol-4-ethanamine

A stirred mixture of 3.2 g of the product of Step B, 5.1 g of potassium carbonate, 3.4 g of 1-iodopropane and 64 ml of acetone was refluxed under an inert atmosphere for 19 hours and the acetone was evaporated. 100 ml of water and 2 ml of sodium hydroxide were added to the mixture which was then extracted 3 times with 50 ml of methylene chloride. The combined organic phases were washed with 100 ml of water, dried over magnesium sulfate and filtered. The filtrate was evaporated to dryness and the 3.6 g of oil residue were chromatographed over silica gel to obtain 900 mg of N-[2-(3-methoxyphenyl)-ethyl]-N-propyl-1H-imidazol-4-ethanamine in the form of a yellow oil which was used as is for the next step. C.C.M. over silica (7-3 $CHCl_3$-Methanol): Rf=0.20.

STEP D:
3-[2-(2-{1H-imidazol-4-yl}-ethyl)propylaminoethyl]-phenol oxalate

A stirred mixture of 800 mg of the product of Step C, 4 ml of acetic acid and 4 ml of 48% hydrobromic acid was refluxed under an inert atmosphere for 90 minutes and was then cooled and mixed with ice. The mixture was made alkaline by addition of concentrated ammonium hydroxide and was extracted 3 times with 20 ml of methylene chloride. The organic phase was dried over magnesium sulfate and was filtered and the filtrate was evaporated to dryness. The 800 mg of yellow oil residue were dissolved in 5 ml of methanol and 365 mg of oxalic acid dihydrate were added thereto. The mixture was heated until dissolution occured and was cooled and vacuum filtered to obtain 600 mg of product melting at 165° C., then 170° C. The product was crystallized twice from methanol to obtain 3-[2-(2-{1H-imidazol-4-yl}-ethyl)-propylaminoethyl]-phenol oxalate melting at 170° C.

Analysis: $C_{18}H_{25}N_3O_5$: molecular weight=363.40:
Calculated: %C 59.49; %H 6.93; %N 11.56; Found: %C 59.0; %H 6.8; %N 11.4

UV Spectrum (ethanol):
    Inflex.—214 nm    $E_1^1=336$    $\epsilon=12,200$
    Max.—274 nm    $E_1^1=56$    $\epsilon=2,050$
    Inflex.—280 nm    $E_1^1=51$ UV Spectrum (ethanol—0.1 N NaOH):
    Max.—240 nm    $E_1^1=267$    $\epsilon=9,700$ Max.—291 nm  $E_1^1=45$   $\epsilon=3,450$

EXAMPLE 7

3-[2-({2-(1H-indol-3-yl)-ethyl}-propylamino)-ethyl]-phenol hydrochloride

STEP A:
3-methoxy-N-[2-(1H-indol-3-yl)-ethyl]-benzeneacetamide

A mixture of 29 g of tryptamine and 30 g of 3-methoxy-phenylacetic acid was heated at 200° C. for one hour and after cooling the mixture to 50° C., the mixture was dissolved in 200 ml of ethyl acetate. The organic phase was washed successively with N hydrochloric acid, with water, with 2 N sodium hydroxide and with water and was dried and evaporated to dryness. The 59 g of red oil were crystallized from ether and the mixture was vacuum filtered. The product was dried to obtain 47.2 g of 3-methoxy-N-[2-(1H-indol-3-yl)-ethyl]-benzeneacetamide in the form of a beige solid melting at 78° C. which was used as is for the next step. A sample recrystallized from ether melted at 82° C.

STEP B:
N-[2-(3-methoxyphenyl)-ethyl]-1H-indol-3-ethanamine hydrochloride 21 ml of a complex of borane-dimethylsulfide (titrating at 1 ml≃1 mmole) were slowly added under an inert atmosphere to a solution of 30.6 g of the compound of Step A in 150 ml of tetrahydrofuran and the mixture was refluxed for 135 minutes and was cooled to 20°–25° C. 150 ml of 2 N hydrochloric acid were slowly added thereto and the mixture was refluxed for 2 hours. Then, the tetrahydrofuran was evaporated and 50 ml of sodium hydroxide solution were added to make the mixture alkaline. The mixture was extracted with ethyl acetate and the organic phase was washed with water, dried over magnesium sulfate and evaporated to dryness. The 32 g of orange oil residue was chromatographed over silica gel and were eluted with an 80-15-5 methylene chloride-methanol-acetic acid mixture to obtain 22 g of an acetate with an Rf=0.37. The product was neutralized with 6 N sodium hydroxide solution and the mixture was extracted with ethyl acetate. The organic phase was washed with water, dried and evaporated to dryness. The 14 g of orange oil residue were dissolved in 70 ml of ethyl acetate and an excess of ethyl acetate saturated with hydrogen chloride was added thereto. The mixture was vacuum filtered and the recovered product was washed with ethyl acetate and dried to obtain 13.95 g of N-[2-(3-methoxyphenyl)-ethyl]-1H-indol-3-ethanamine hydrochloride in the form of a beige product melting at 164° C., then 177° C. which was used as is for the next step.

STEP C:
N-[2-(3-methoxyphenyl)-ethyl]-N-propyl-1H-indol-3-ethanamine hydrochloride The product of Step B was empasted with 100 ml of water and then an excess of ammonium hydroxide was added thereto. The mixture was extracted with ethyl acetate and to dryness. The 13 g of orange oil residue were dissolved in 200 ml of acetone and 29.3 g of potassium carbonate and 9.6 ml of 1-iodopropane were added thereto. The mixture was refluxed for 6 hours and was filtered and the filtrate was evaporated to dryness. The residue was taken up in 100 ml of 2 N sodium hydroxide solution and the mixture was extracted with ethyl acetate. The organic phase was washed with water, dried and evaporated to dryness. The 15 g of orange oil residue were dissolved in 80 ml of ethyl acetate and an excess of ethyl acetate saturated with hydrogen chloride was added thereto. After crystallization, the mixture was concentrated and placed in a refrigerator overnight. The mixture was vacuum filtered and the recovered product was washed with ethyl acetate and dried to obtain 12.6 g of N-[2-(3-methoxyphenyl)-ethyl]-N-propyl-1H-indol-3-ethanamine hydrochloride melting at 140° C.

STEP D:
3-[2-{2-(1H-indol-3-yl)-ethyl}-propylamino)-ethyl]-phenol hydrochloride The product of Step C was empasted with 50 ml of water and an excess of ammonium hydroxide was added thereto. The mixture was extracted with ethyl acetate and the organic phase was washed with water, dried and evaporated to dryness. The 11.55 g of orange oil residue were added to 45 g of pyridine and the mixture was refluxed at 220° C. under an inert atmosphere for 135 minutes. The mixture was cooled to 20° C. and was made alkaline with ammonium hydroxide. The mixture was then extracted with ethyl acetate and the organic phase was washed with water, dried and evaporated to dryness. The 12.8 g of reddish oil residue were dissolved in 60 ml of isopropanol and an excess of ethyl acetate saturated with hydrogen chloride was added thereto. The ethyl acetate was distilled and crystallization was induced after which the mixture was held overnight in a refrigerator. The mixture was vacuum filtered and the recovered product was washed with isopropanol and dried to obtain 9.3 g of 3-[2-({2-(1H-indol-3-yl)-ethyl}-propylamino)-ethyl]-phenol hydrochloride in the form of a clear beige solid melting at 192° C., then 197° C. Crystallization of the product from ethanol yielded a product melting at 198° C.

Analysis: $C_{21}H_{26}N_2O$ . HCl; molecular weight=358.90 Calculated: %C 70.28; %H 7.58; %N 7.80; %Cl 9.88; Found: %C 70.3; %H 7.7; %N 7.5; %Cl 10.1

UV Spectrum (ethanol):
  Max.—220 nm  $E_1^1=1149$  $\epsilon=41,200$
  Max.—274 nm  $E_1^1=214$
  Max.—280 nm  $E_1^1=220$  $\epsilon=7,900$
  Max.—289 nm  $E_1^1=155$  $\epsilon=5,550$
  Max.—362 nm  $E_1^1=3$
  Max.—380 nm  $E_1^1=4$
  Max.—403 nm  $E_1^1=3.5$ UV Spectrum (ethanol-0.1 NaOH):
  Inflex.—240 nm  $E_1^1=305$  $\epsilon=10,950$
  Inflex.—275 nm  $E_1^1=190$
  Max.—284 nm  $E_1^1=232$  $\epsilon=8,300$
  Max.—290 nm  $E_1^1=233$  $\epsilon=8,400$
  Inflex.—295 nm  $E_1^1=166$  $\epsilon=5,950$

EXAMPLE 8

Tablets were prepared containing either 10 mg of 3-{[2-(cyclohexylethyl)-propylamino]-ethyl}-phenol hydrochloride or 3-[2-{propyl-(2-(2-thienyl)-ethyl]-amino}-ethyl]-phenol hydrochloride and sufficient excipient of lactose, starch, talc and magnesium stearate for a final weight of 200 mg.

PHARMACOLOGICAL DATA

A. Rotation after unilateral injury to nigrostriated fasciculus with 6-hydroxydopamine The test was conducted on groups of 6 male rats weighing about 250 g and the injury was caused by injection in the dark substance of 8 μg of 6-hydroxydopamine hydrochloride dissolved in 4 μl of physiological serum containing 1 mg/ml of ascorbic acid [U Ungerstedt, Acta physiol. Scand., Vol. 82 (1971), supp. 367, p. 69–93]. The test compounds were administered orally or intraperitoneally and the animals were individually placed in a rotometer which counted the number of rotations of each animal in 2 ways. Each test lasted for 90 minutes and under these conditions, the compounds of Examples 2,3,5 and 7 showed contralateral rotations at a dose of 0.5, 2.5 and 10 mg/kg, respectively when administered intraperitoneally. These results show that the tested compounds possess interesting dopaminergic stimulating activity.

B. Acute toxicity

The 50% lethal dose ($DL_{50}$) was determined for the products after intraperitoneal administration to mice and the mortality was determined 48 hours after the administration of the test product. The $DL_{50}$ for product of Example 1 was greater than 200 mg/kg and for compound 2 was chart 150 mg/kg.

Various modifications of the products and methods of the invention may be made without departing from the spirit or scope thereof and it is to be understood that the invention is to be limited only as defined in the appended claims.

We claim:

1. A compound selected from the group consisting of 3-(aminoethyl)-phenols of the formula

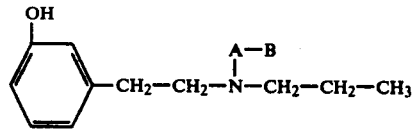

wherein A is a simple bond or alkylene of 1 to 6 carbon atoms and B is selected from the group consisting of phenyl, and thienyl with the proviso that B is not phenyl when A is ethylene and their non-toxic, pharmaceutically acceptable acid addition salts.

2. A compound of claim 1 wherein A is a simple bond or alkylene of 2 to 3 carbon atoms.

3. A compound of claim 1 wherein -A-B is selected from the group consisting of phenylpropyl and 2-(2-thienyl)-ethyl.

4. A compound of claim 1 which is di-[3-{2-[(3-phenylpropyl)-propylamino]-ethyl}-phenol]oxalate.

5. A compound of claim 1 which is 3-[2-propyl-2-(2-thienyl)-ethylamino]-ethyl-phenol hydrochloride.

6. A dopaminergic composition comprising a dopaminergically effective amount of at least one compound of claim 1 and an excipient.

7. A composition of claim 6 wherein B is selected from the group consisting of phenyl and thienyl.

8. A composition of claim 7 wherein A is a simple bond or alkylene of 2 to 3 carbon atoms.

9. A composition of claim 6 wherein -A-B is selected from the group consisting of phenylpropyl and 2-(2-thienyl)-ethyl.

10. A composition of claim 6 wherein the compound is di-[3-}2-[(3-phenylpropyl)-propylamino]-ethyl}-phenol]oxalate.

11. A composition of claim 6 wherein the compound is 3-[2-propyl-2-(2-thienyl)-ethylamino]-ethyl-phenol hydrochloride.

12. A method of inducing dopaminergic activity in warm-blooded animals comprising administering to warm-blooded animals a dopaminergically effective amount of at least one compound of claim 1.

13. A method of claim 12 wherein B is selected from the group consisting of phenyl and thienyl.

14. A method of claim 13 wherein A is a simple bond or alkylene of 2 to 3 carbon atoms.

15. A method of claim 12 wherein -A-B is selected from the group consisting of phenylpropyl and 2-(2-thienyl)-ethyl.

16. A method of claim 12 wherein the compound is di-[3-}2-[(3-phenylpropyl)-propylamino]-ethyl}-phenol]oxalate.

17. A method of claim 12 wherein the compound is 3-[2-propyl-2-(2-thienyl)-ethylamino]-ethyl-phenol hydrochloride.

* * * * *

UNITED STATES PATENT AND TRADEMARK OFFICE
CERTIFICATE OF CORRECTION

PATENT NO. : 4,242,355
DATED : December 30, 1980
INVENTOR(S) : LUCIEN NEDELEC ET AL.

It is certified that error appears in the above—identified patent and that said Letters Patent is hereby corrected as shown below:

Column 3, line 59: "formula" should read -- formulae --.

Column 9, line 66: "200 ml" should read -- 220 ml --.

Column 13, line 61: After "acetate and" insert

-- the organic phase was washed with water, dried and evaporated --.

Signed and Sealed this

Sixteenth Day of June 1981

[SEAL]

Attest:

RENE D. TEGTMEYER

Attesting Officer    Acting Commissioner of Patents and Trademarks